(12) United States Patent
Cutler et al.

(10) Patent No.: US 9,913,409 B2
(45) Date of Patent: Mar. 6, 2018

(54) INTRUSION DETECTION FOR SUBMERGED DATACENTERS

(71) Applicant: Microsoft Technology Licensing, LLC, Redmond, WA (US)

(72) Inventors: Benjamin F. Cutler, Seattle, WA (US); Norman Ashton Whitaker, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 15/167,808

(22) Filed: May 27, 2016

(65) Prior Publication Data

US 2016/0378981 A1 Dec. 29, 2016

Related U.S. Application Data

(63) Continuation of application No. 14/752,669, filed on Jun. 26, 2015, and a continuation of application No. 14/752,676, filed on Jun. 26, 2015.
(Continued)

(51) Int. Cl.
*H04B 13/02* (2006.01)
*H05K 7/20* (2006.01)
(Continued)

(52) U.S. Cl.
CPC ....... *H05K 7/20836* (2013.01); *A01K 29/005* (2013.01); *A01K 67/033* (2013.01); *F24F 5/0046* (2013.01); *F25D 1/02* (2013.01); *F28D 1/022* (2013.01); *F28D 15/00* (2013.01); *G06F 21/554* (2013.01); *G08B 13/2491* (2013.01); *H05K 7/1495* (2013.01); *H05K 7/1497* (2013.01); *H05K 7/2079* (2013.01);
(Continued)

(58) Field of Classification Search
CPC ............. H05K 7/20836; H05K 7/1495; A01K 29/005; A01K 67/033; F24F 5/0046; F25D 1/02; F28D 1/022
See application file for complete search history.

(56) References Cited

U.S. PATENT DOCUMENTS 1,757,174 A 6/1930 Douglas
2,870,729 A 1/1959 Shannon et al.
(Continued)

FOREIGN PATENT DOCUMENTS

CN 201846435 U 5/2011
DE 102011115657 A1 3/2013
(Continued)

OTHER PUBLICATIONS

Markoff, John, "Microsoft Plumbs Ocean's Depths to Test Underwater Data Center", Published on: Jan. 31, 2016, 5 pages. Available at: http://www.nytimes.com/2016/02/01/technology/microsoft-plumbs-oceans-depths-to-test-underwater-data-center.html?_r=2.
(Continued)

*Primary Examiner* — Joseph Feild
*Assistant Examiner* — Rufus Point

(57) ABSTRACT

Examples of the disclosure provide a datacenter configured for operation while submerged in water. The datacenter includes one or more physically separable modules. The datacenter also includes an intrusion detection system that has one or more intrusion detection modules.

19 Claims, 10 Drawing Sheets

Related U.S. Application Data

(60) Provisional application No. 62/286,961, filed on Jan. 25, 2016, provisional application No. 62/286,964, filed on Jan. 25, 2016.

(51) Int. Cl.
  *F28D 1/02* (2006.01)
  *F24F 5/00* (2006.01)
  *F25D 1/02* (2006.01)
  *F28D 15/00* (2006.01)
  *A01K 29/00* (2006.01)
  *A01K 67/033* (2006.01)
  *H05K 7/14* (2006.01)
  *G06F 21/55* (2013.01)
  *G08B 13/24* (2006.01)
  *F28D 21/00* (2006.01)

(52) U.S. Cl.
  CPC ..... *H05K 7/20236* (2013.01); *H05K 7/20709* (2013.01); *F28D 2021/0028* (2013.01); *G06F 2221/034* (2013.01)

(56) References Cited

U.S. PATENT DOCUMENTS

| | | | | |
|---|---|---|---|---|
| 3,419,849 A * | 12/1968 | Anderson | G05F 1/569 | 710/49 |
| 4,411,213 A | 10/1983 | Laukien | | |
| 4,781,023 A * | 11/1988 | Gordon | F03B 13/20 | 290/42 |
| 4,862,427 A * | 8/1989 | Almagor | G01S 7/003 | 367/100 |
| 5,049,004 A * | 9/1991 | Niimura | E02D 23/02 | 405/194 |
| 5,511,504 A | 4/1996 | Martin | | |
| 5,969,608 A * | 10/1999 | Sojdehei | G08B 13/1663 | 340/539.1 |
| 6,020,653 A * | 2/2000 | Woodbridge | F03B 13/1865 | 290/42 |
| 6,100,600 A * | 8/2000 | Pflanz | F03D 13/25 | 290/4 R |
| 6,186,702 B1 | 2/2001 | Bartkowski | | |
| 6,559,552 B1 * | 5/2003 | Ha | F03B 13/00 | 290/54 |
| 6,765,487 B1 * | 7/2004 | Holmes | B63G 13/00 | 340/541 |
| 6,813,897 B1 * | 11/2004 | Bash | F25B 27/00 | 307/64 |
| 6,833,631 B2 * | 12/2004 | Van Breems | F03B 13/1845 | 204/194 |
| 6,953,328 B2 * | 10/2005 | Welch, Jr. | F04B 35/004 | 417/331 |
| 7,059,123 B2 * | 6/2006 | Welch, Jr. | F03B 13/187 | 299/53 |
| 7,105,939 B2 * | 9/2006 | Bednyak | B60L 8/00 | 290/1 R |
| 7,257,946 B2 * | 8/2007 | Welch, Jr. | F03B 13/1875 | 290/53 |
| 7,269,751 B2 * | 9/2007 | Janakiraman | G06F 1/263 | 713/323 |
| 7,331,174 B2 * | 2/2008 | Welch, Jr. | E02B 9/08 | 290/53 |
| 7,453,165 B2 * | 11/2008 | Hench | F03B 13/20 | 290/42 |
| 7,484,668 B1 * | 2/2009 | Eiler | F24F 3/16 | 236/49.3 |
| 7,525,207 B2 * | 4/2009 | Clidaras | F03B 13/1885 | 290/42 |
| 7,724,513 B2 * | 5/2010 | Coglitore | H05K 7/20745 | 165/104.33 |
| 7,864,530 B1 * | 1/2011 | Hamburgen | H05K 7/20827 | 165/104.33 |
| 8,193,651 B2 * | 6/2012 | Lightfoot | F03B 13/20 | 290/42 |
| 8,201,266 B2 * | 6/2012 | Campbell | G08B 13/19 | 361/754 |
| 8,471,397 B2 * | 6/2013 | Iglesias Rodriguez | F03B 13/144 | 290/42 |
| 8,549,869 B1 | 10/2013 | Whitted et al. | | |
| 8,564,151 B1 * | 10/2013 | Huebner | F03B 17/063 | 290/42 |
| 8,595,515 B1 * | 11/2013 | Weber | G06F 1/3206 | 713/300 |
| 8,601,287 B1 * | 12/2013 | Weber | G06F 1/3206 | 702/186 |
| 8,636,565 B2 | 1/2014 | Carlson et al. | | |
| 8,700,929 B1 * | 4/2014 | Weber | G06F 1/3206 | 713/300 |
| 8,774,980 B2 * | 7/2014 | Chang | G05D 23/1931 | 361/679.34 |
| 8,780,542 B1 * | 7/2014 | Dariavach | H01L 23/34 | 290/1 R |
| 8,839,254 B2 * | 9/2014 | Horvitz | G06F 9/4893 | 718/102 |
| 8,849,469 B2 * | 9/2014 | Belady | G06Q 10/06312 | 700/291 |
| 8,853,872 B2 * | 10/2014 | Clidaras | F03B 13/20 | 290/43 |
| 8,854,809 B2 * | 10/2014 | Neumann | G06F 1/20 | 361/679.54 |
| 8,890,359 B2 * | 11/2014 | Chang | G06F 1/263 | 307/43 |
| 8,913,383 B1 | 12/2014 | Goldsmith et al. | | |
| 9,009,500 B1 * | 4/2015 | Fan | G06F 9/50 | 713/300 |
| 9,016,352 B2 * | 4/2015 | Helbig | F28F 9/007 | 165/67 |
| 9,063,738 B2 * | 6/2015 | Jain | G06F 1/329 | |
| 9,089,078 B2 * | 7/2015 | Branton | H05K 7/20754 | |
| 9,155,230 B2 * | 10/2015 | Eriksen | H05K 7/20781 | |
| 9,207,993 B2 * | 12/2015 | Jain | G06F 9/5094 | |
| 9,209,985 B1 * | 12/2015 | Wise | H04L 41/147 | |
| 9,287,710 B2 * | 3/2016 | Talkin | G06Q 50/06 | |
| 9,310,855 B2 * | 4/2016 | Godrich | G06F 1/20 | |
| 9,342,375 B2 * | 5/2016 | Hyser | G06F 9/5094 | |
| 9,439,322 B1 * | 9/2016 | Magcale | H05K 7/20781 | |
| 9,439,330 B1 * | 9/2016 | Wu | H05K 7/2079 | |
| 9,439,331 B1 * | 9/2016 | Wu | H05K 7/2079 | |
| 9,450,838 B2 * | 9/2016 | Jain | G06F 9/5072 | |
| 9,595,054 B2 * | 3/2017 | Jain | G06F 9/5072 | |
| 9,648,777 B2 * | 5/2017 | Finn | H05K 7/1497 | |
| 9,653,003 B2 * | 5/2017 | Laine | G09B 29/10 | |
| 9,655,283 B2 * | 5/2017 | James | H05K 7/20709 | |
| 2007/0281639 A1 * | 12/2007 | Clidaras | G06F 1/20 | 455/128 |
| 2008/0029250 A1 * | 2/2008 | Carlson | F24F 11/0001 | 165/104.33 |
| 2008/0055846 A1 * | 3/2008 | Clidaras | G06F 1/20 | 361/679.41 |
| 2008/0055850 A1 | 3/2008 | Carlson et al. | | |
| 2008/0209234 A1 * | 8/2008 | Clidaras | F03B 13/1885 | 713/300 |
| 2009/0078401 A1 | 3/2009 | Cichanowicz | | |
| 2009/0216910 A1 * | 8/2009 | Duchesneau | G06F 9/5072 | 709/250 |
| 2009/0229194 A1 | 9/2009 | Armillas | | |
| 2009/0293136 A1 * | 11/2009 | Campbell | G08B 13/189 | 726/34 |
| 2009/0295167 A1 | 12/2009 | Clidaras et al. | | |
| 2009/0297270 A1 | 12/2009 | Black et al. | | |
| 2010/0277719 A1 * | 11/2010 | Chen | G08B 13/186 | 356/73.1 |
| 2011/0132579 A1 | 6/2011 | Best et al. | | |
| 2011/0144930 A1 * | 6/2011 | Bruno | G01S 3/801 | 702/56 |
| 2011/0154842 A1 | 6/2011 | Heydari et al. | | |
| 2011/0240497 A1 | 10/2011 | Dechene et al. | | |
| 2011/0247348 A1 | 10/2011 | Mashiko et al. | | |

(56) References Cited

U.S. PATENT DOCUMENTS

| | | | |
|---|---|---|---|
| 2012/0027154 A1* | 2/2012 | Sugiura | G21C 17/01 376/249 |
| 2012/0232879 A1 | 9/2012 | Iyengar et al. | |
| 2013/0044426 A1 | 2/2013 | Neumann et al. | |
| 2013/0058029 A1 | 3/2013 | Ootani et al. | |
| 2013/0125825 A1 | 5/2013 | Kania et al. | |
| 2013/0190941 A1 | 7/2013 | Cader et al. | |
| 2014/0192708 A1* | 7/2014 | Wise | H04B 7/18513 370/316 |
| 2015/0194813 A1* | 7/2015 | Finn | H05K 7/1497 307/19 |
| 2015/0321739 A1 | 11/2015 | Dehlsen | |
| 2015/0382511 A1* | 12/2015 | James | H05K 7/20709 361/679.46 |
| 2015/0382515 A1 | 12/2015 | James et al. | |
| 2016/0012713 A1* | 1/2016 | Siwak | G08B 13/22 340/541 |
| 2016/0266246 A1* | 9/2016 | Hjelmstad | G01S 17/023 |
| 2016/0286695 A1* | 9/2016 | Wu | H05K 7/20772 |
| 2016/0381835 A1* | 12/2016 | Cutler | F24F 5/0046 361/679.46 |
| 2017/0023384 A1* | 1/2017 | Young | G01D 5/268 |

FOREIGN PATENT DOCUMENTS

| | | |
|---|---|---|
| EP | 2891761 A2 | 7/2015 |
| GB | 2240847 A | 8/1991 |
| WO | 2008039181 A1 | 4/2008 |
| WO | 2009108070 A1 | 9/2009 |
| WO | 2012129612 A1 | 10/2012 |
| WO | 2013184820 A1 | 12/2013 |
| WO | 2014120275 A1 | 8/2014 |

OTHER PUBLICATIONS

Callahan, Emily, "Artificial Reefing—The Blue Solution to America's Aging Infrastructure?", Published on: Nov. 6, 2014, 9 pages. Available at: http://voices.nationalgeographic.com/2014/11/06/artificial-reefing-the-blue-solution-to-americas-aging-infrastructure/.

Matteson, et al., "Maximizing Data Center Energy Efficiency by Utilizing New Thermal Management and Acoustic Control Methodology", In International Technical Conference and Exhibition on Packaging and Integration of Electronic and Photonic Microsystems, vol. 2, Jul. 16, 2013, 1 page.

Toma, et al., "Study on Heat Dissipation and Cooling Optimization of the Junction Box of OBSEA Seafloor Observatory", In Proceedings of IEEE/ASME Transactions on Mechatronics, vol. 20, Issue 3, Jun. 2015, pp. 1301-1309.

"Second Written Opinion Received for PCT Application No. PCT/U52015/037847", dated Jun. 1, 2016, 7 pages.

"International Preliminary Report on Patentability Received for PCT Application No. PCT/US2015/037847", dated Sep. 21, 2016, 6 pages.

"International Preliminary Report on Patentability Issued in PCT Application No. PCT/US2015/037848" dated Apr. 21, 2016, 6 pages.

Masaki, et al., "Underwater Surveillance System to Counteract Associated Underwater Threats", In NEC Technical Journal, vol. 8, Issue 1, Sep. 2013, pp. 63-67.

Felemban, Emad, "Advanced Border Intrusion Detection and Surveillance Using Wireless Sensor Network Technology", In International Journal of Communications, Network and System Sciences, vol. 6, Issue 5, May 2013, pp. 251-259.

Casari, Paolo, "Using Sound to create Underwater Networks", Published on: May 29, 2015, 3 pages. Available at: http://phys.org/wire-news/194344776/using-sound-to-create-underwater-networks.html.

Murad, et al., "A Survey on Current Underwater Acoustic Sensor Network Applications", In International Journal of Computer Theory and Engineering, vol. 7, Issue 1, Feb. 2015, pp. 51-56.

Laumer, John, "Google Floats a Data Center Patent: Offshore, Ocean-Cooled, Wave-Powered, and Modular", Published on: Sep. 20, 2008, 4 pages. Available at: http://www.treehugger.com/corporate-responsibility/google-floats-a-data-center-patent-offshore-ocean-cooled-wave-powered-and-modular.html.

Fletcher, Joanna, "What Happened to Google's Floating Data Center?", Published on: Dec. 4, 2010, 2 pages. Available at: http://www.hostway.com/web-resources/find-web-hosting/what-happened-to-googles-floating-data-center/.

Cutler, "Intrusion Detection for Submerged Datacenters" U.S. Appl. No. 62/286,961, 29 pages.

Cutler, et al., "Artificial Reef Datacenter" U.S. Appl. No. 62/286,964, 19 pages.

Trabish, Herman K., "Ocean Energy to Power Google's Sea-Going Data Center", Published on: Sep. 10, 2008, 4 pages. Available at: http://newenergynews.blogspot.in/2008/09/ocean-energy-to-power-googles-sea-going.html.

Miller, Rich, "Google Planning Offshore Data Barges", Published on: Sep. 6, 2008, 5 pages Available at: http://www.datacenterknowledge.com/archives/2008/09/06/google-planning-offshore-data-barges/.

Miller, Rich, "Data Centers on Cargo Ships?", Published on: Jan. 8, 2008, 5 pages Available at: http://www.datacenterknowledge.com/archives/2008/01/08/data-centers-on-cargo-ships/.

"International Search Report & Written Opinion Received for PCT Application No. PCT/US2015/037848" dated Oct. 6, 2015, 10 pages.

Patel, et al., "Thermal Considerations in Cooling Large Scale High Compute Density Data Centers", In the Eighth Intersociety Conference on Thermal and Thermomechanical Phenomena in Electronic Systems, May 2002, 10 pages.

U.S. Appl. No. 13/917,636, Rubenstein, et al., "Renewable Energy Based Datacenter Cooling", filed Jun. 13, 2013, 31 pages.

Office Action Summary, U.S. Appl. No. 14/272,656, Notificaion Date: Nov. 30, 2015, 12 pages.

Green (Low Carbon) Data Center Blog, The Under Water Data Center, Response to Risks of Google's Floating Data Center, Submerge, Sep. 12, 2008, 3 pages. Available at:. http://www.greenm3.com/gdcblog/2008/9/12/the-under-water-data-center-response-to-risks-googlersquo.html.

U.S. Appl. No. 14/272,656, Dehlsen, "Marine Subsurface Data Center Vessel", filed May 8, 2014, 16 pages.

"International Search Report & Written Opinion Received for PCT Application No. PCT/US2015/037847", dated Nov. 9, 2015, 11 pages.

"International Search Report and Written Opinion Issued in PCT Application No. PCT/US2017/013621", dated Apr. 13, 2017, 14 Pages.

* cited by examiner

INTRUSION DETECTION FOR SUBMERGED DATACENTERS

CLAIM OF PRIORITY

This application claims the benefit of U.S. Provisional Patent Application Ser. No. 62/286,961, entitled "Intrusion Detection for Submerged Datacenters" and filed on Jan. 25, 2016, and U.S. Provisional Patent Application Ser. No. 62/286,964, entitled "Artificial Reef Datacenter" and filed on Jan. 25, 2016, U.S. patent application Ser. No. 14/752,669, entitled "Underwater Container Cooling Via Integrated Heat Exchanger" and filed on Jun. 26, 2015, and U.S. patent application Ser. No. 14/752,676, entitled "Underwater Container Cooling Via External Heat Exchanger" and filed on Jun. 26, 2015, all of which are incorporated herein by reference in their entirety for all intents and purposes.

SUMMARY

This Summary is provided to introduce a selection of representative concepts in a simplified form that are further described below in the Detailed Description. This Summary is not intended to identify key features or essential features of the claimed subject matter, nor is it intended to be used in any way that would limit the scope of the claimed subject matter.

Briefly, one or more of various aspects of the subject matter described herein are directed towards a datacenter configured for operation while submerged in water. The datacenter includes one or more physically separable modules. The system also includes an intrusion detection system that has one or more intrusion detection sensors.

BRIEF DESCRIPTION OF THE DRAWINGS

The present disclosure is illustrated by way of example and not limited in the accompanying figures in which like reference numerals indicate similar elements and in which.

DETAILED DESCRIPTION

Figure 1:
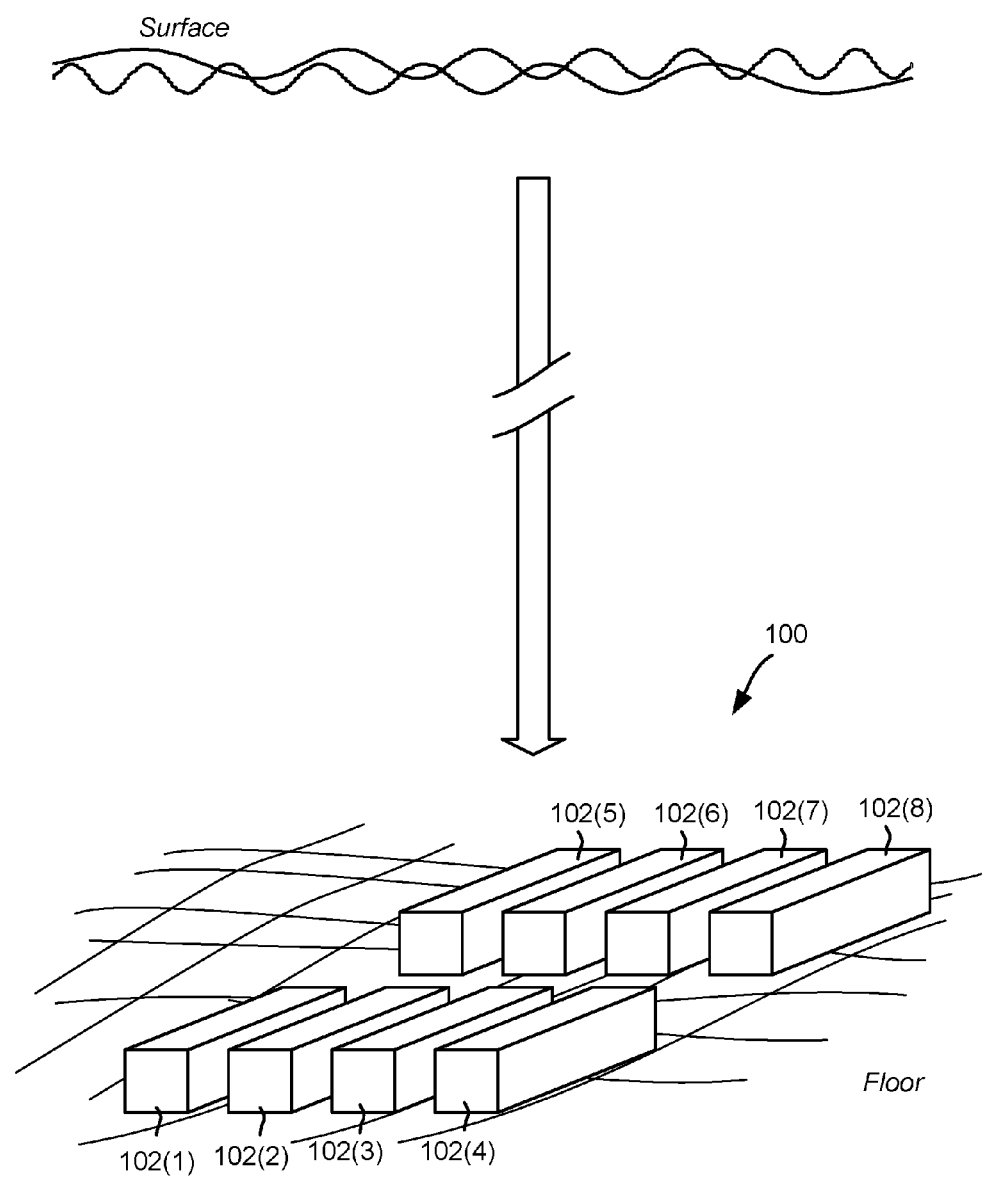
FIG. 1 is an example representation of a submerged datacenter (configured in a plurality of modules) resting on the floor of a body of water, according to one or more example implementations.

As cloud-based computing and cloud-based services grow, datacenters need to be provided to serve client customers. Customers want fast speeds (lowest possible latency) for their cloud applications. In order to satisfy customers, future datacenters need to be positioned as close as possible to the customer base, such as submerged in nearby bodies of water. At the same time, consideration needs to be given to privacy and security of the data contained in the datacenter.

Because datacenters may contain large amounts of valuable data, they are subject to intrusion. Submerged, or subsea datacenters may be subject to intrusion by unwanted natural or man-made phenomena, in particular divers, submarines, ROVs, trained sea mammals, capture devices, or other covert attempts to access the datacenter.

Briefly, examples of the disclosure provide a datacenter configured for operation while submerged in water. The datacenter includes one or more physically separable modules. The datacenter also includes an intrusion detection system that has one or more intrusion detection modules.

Another aspect of the disclosure is directed toward a method for detecting intrusion into a datacenter submerged in water. The method includes receiving data from a plurality of sensors. The method also includes processing the data received from the plurality of sensors to identify an anomaly that suggests a change in the environment. Moreover, the method includes initiating a search for an entity responsible for the anomaly, and identifying the entity by use of the plurality of sensors and an external database.

Yet another aspect of the disclosure is directed to a method for performing protective actions upon detection of an intrusion into a datacenter submerged in water. The method includes alerting network operations, broadcasting warnings into the surrounding environment, and ceasing network traffic. In addition, the datacenter will failover to a geo-replicated copy of the datacenter. The method also includes rendering all in-datacenter data inaccessible and rendering all local data inaccessible.

The present disclosure is generally directed towards providing monitoring and intrusion detection of subsea equipment, such as centrally managed computing resources and related support systems. More particularly, the subsea equipment may include a datacenter that is designed to be submerged, for example on the ocean floor or the floor of any body of water, such as a lake, a river, a flooded former quarry, and the like. The datacenter may be deployed relatively close to current and potential customers, and positioned in a way to take advantage of sustainable power that is also environmentally friendly and the massive heat sink provided by the water. By positioning the datacenter in deep water, such as anchoring it or sinking it to the ocean floor, the risks of umbilical detachment or damage to the datacenter by external forces are significantly reduced. To carry out monitoring of the equipment during subsea operations, various measurements may be obtained from the equipment and the operating environment using one or more sensors. Some of these sensors may be acoustic sensors, optical sensors, and vibration sensors used to monitor the behavior, condition, and operations of the equipment and the surrounding environment.

It should be understood that any of the examples herein are non-limiting. For example, ocean-submerged datacenters are exemplified, as is the concept of positioning datacenters on the ocean floor, e.g., by sinking them. However, bodies of water other than the ocean provide similar benefits, and anchoring rather than sinking may be used, such as if the ocean floor is too uneven at an otherwise desired location. As used herein, "floor" refers to the bottom of any body of water, e.g., the ocean floor, a riverbed, seabed, lake bottom and so on. As such, the present disclosure is not limited to any particular embodiments, aspects, concepts, structures, functionalities or examples described herein. Rather, any of the embodiments, aspects, concepts, structures, functionalities or examples described herein are non-limiting, and the present disclosure may be used in various ways that provide benefits and advantages in datacenters and computing in general.

As generally represented in the example implementation of FIG. 1, a number of (e.g., modular) datacenter modules 102(1)-102(8) may be submerged to rest on the floor of any body of water. The datacenter modules 102(1)-102(8) are coupled together to form a datacenter 100. Modularity is not necessary, however modularity has some advantages, including being able to size the datacenter 100 to different populations by using an appropriate number of modules, replacement of a module at the end of the module lifecycle, portability, security (e.g., modules may be divided into public modules or private modules, with no communication between them), and so on. Further, modularity allows for ease of manufacturing; it may take an extended period of time to develop and deploy a custom datacenter, which may be disadvantageous in many situations, and modularity may speed up the deployment while lowering the price.

With respect to deployment, datacenter modules 102(1)-102(8) may be towed or otherwise conveyed to a desired location, coupled to cabling (not shown) and other datacenter modules 102(1)-102(8), and sank. Sinking of the datacenter modules 102(1)-102(8) may be accomplished in any number of ways, such as by attaching a weight, adding water to a ballast tank, and so forth. In the event that the datacenter modules 102(1)-102(8) may need service or replacement, the weight may be removed to enable the datacenter modules 102(1)-102(8) to float. Note that at depths below conventional human diving capability, machinery may be used to remove the weight or attach a pipe to pump air in and the water out of the ballast tank. Similarly, any components that are more likely to need servicing, such as those with moving parts like pumps, may employ redundancy and/or be designed to be externally detachable.

As is understood, the depiction of eight datacenter modules 102(1)-102(8) in FIG. 1 is an arbitrary number merely for purposes of illustration. For example, a single datacenter may be submerged (which need not be modular), or any practical number may be submerged.

Cabling is not shown in FIG. 1, but as is understood, a power source and data communication connections are coupled to each datacenter module 102(1)-102(8). Moreover, any or all of the datacenter modules 102(1)-102(8) may be coupled to one another for highly efficient internal communication including by any wired or wireless connections. In the event that power is coming from land, the cabling may be arranged such that a single jacket surrounds both the power cable and fiber optic communication cabling, whereby only one reel need be used, and the different cables cannot get in each other's way during deployment. Further, at least some of the communication signals may be transmitted/received through the power cable.

It is noted that in general, the deeper the datacenter 100 is submerged, the less vulnerable the datacenter 100 is to various risks, such as unwanted natural or man-made phenomena, in particular divers, submarines, ROVs, trained sea mammals, capture devices, or other covert attempts to access the submerged datacenter. Due to their accessibility, land-based datacenters are often easier targets for covert attempts to physically access the datacenter. A submerged datacenter reduces a threat of unwanted physical access by nature of the reduced accessibility.

Note that a partially-submerged datacenter and/or one submerged in relatively shallow water is susceptible to ocean currents, fishing nets, anchors, and submarines in a manner that risks impact or detachment from its source of power and internet. Notwithstanding, in some situations a partially-submerged datacenter and/or one submerged in relatively shallow water may be desirable, and thus the technology described herein as "submerged" also applies to partially-submerged datacenters and/or datacenters submerged in relatively shallow water. As but one example, a datacenter may be partially submerged or submerged in relatively shallow water above or below a waterfall; the waterfall may provide the power, and the submersion the cooling.

Figure 2:
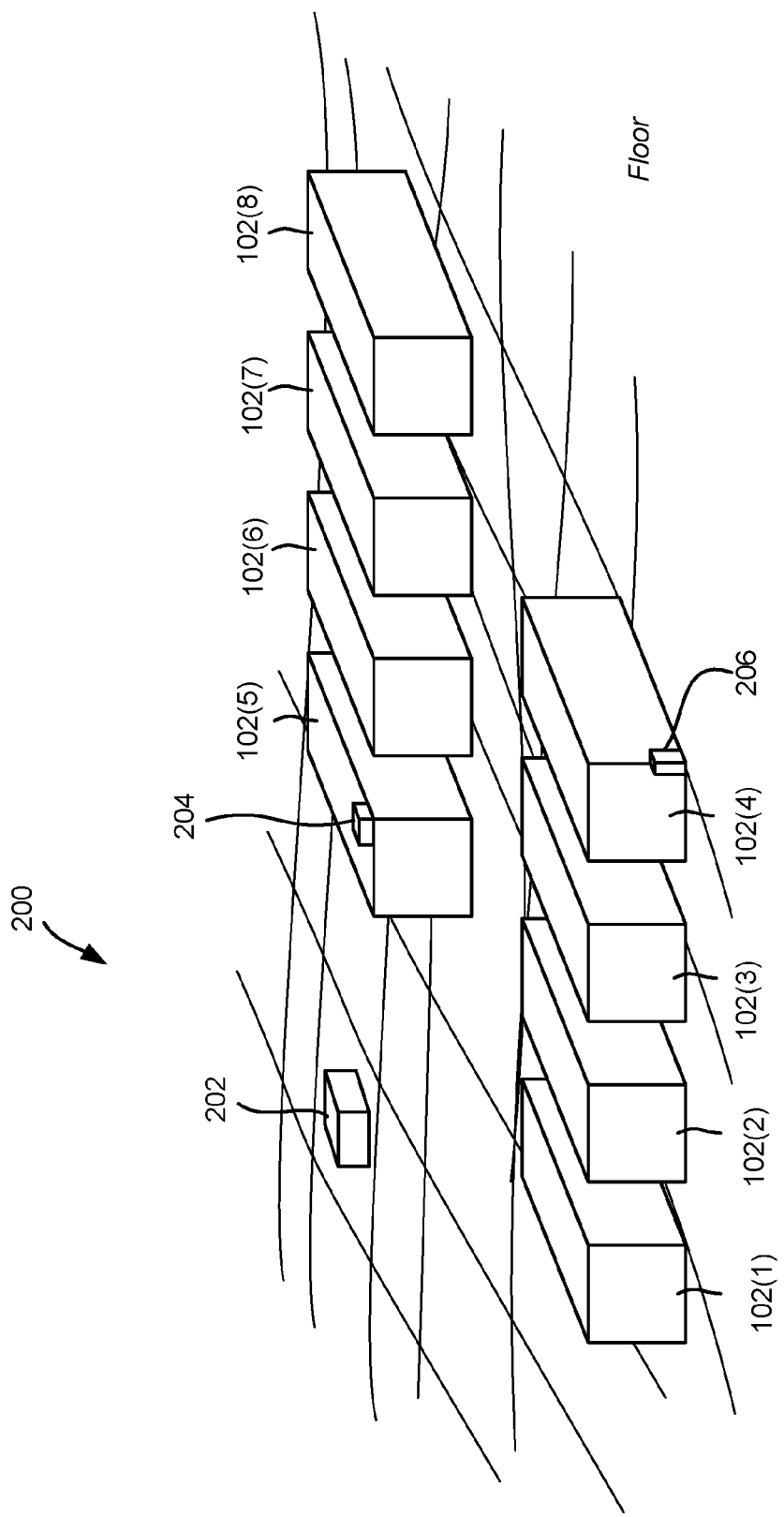
FIG. 2 is a perspective view illustrating an intrusion detection system 200 incorporated into the submerged datacenter 100 shown in FIG. 1.

FIG. 2 is a perspective view illustrating an intrusion detection system 200 incorporated into the submerged datacenter 100 shown in FIG. 1. The intrusion detection system 200 includes at least one intrusion detection module 202, 204, 206, which may be used in whole or in part for intrusion detection. An intrusion detection module, as used herein, may be an integrated module incorporating one or more sensors, which may be one or more heterogeneous sensors (e.g. one or more different types of sensors, such as a sonar sensor and a temperature sensor for example), one or more homogeneous sensors (one or more sensors of the same type, such as multiple cameras for example), or a combination of one or more heterogeneous and one or more homogenous sensors. One or more integrated sensor modules may be implemented at various locations at or adjacent to the submerged datacenter in order to monitor a surrounding environment and detect underwater intrusion attempts. In the exemplary embodiment, the intrusion detection system 200 includes three intrusion detection modules. It is contemplated, however, that the intrusion detection system 200 may include any number of intrusion detection modules that enable the intrusion detection system 200 to function as described herein. Each intrusion detection module 202, 204, 206 may be located near, within, or on a respective one of the datacenter modules 102(1)-102(8).

In the exemplary embodiment, intrusion detection module 202 is a separate module that serves only to sense the environment surrounding the datacenter 100. In other suitable embodiments, intrusion detection module 202 may be a remote module coupled to a respective one of the datacenter modules 102(1)-102(8). As is illustrated in FIG. 2, intrusion detection module 204 is placed onto or adjacent to datacenter module 102(5) such that it is not enclosed within the datacenter module. Intrusion detection module 206, however, is illustrated as being located within datacenter module 102(4). It is contemplated that any number of intrusion detection module, in any configuration, may be included in intrusion detection system 200.

For instance, in some examples, intrusion detection system 200 may include a perimeter barrier (not shown) surrounding the submerged datacenter, with one or more of the intrusion detection modules implemented on or within, or coupled to, the perimeter barrier. As one example, a perimeter barrier may be a seafloor perimeter fence, which may impede objects within an underwater environment from approaching and/or coming into contact with the submerged datacenter, or otherwise detect underwater intrusion attempts of the submerged datacenter. In this example, a perimeter fence may snag or capture objects, such as anchors or other objects being dragged by ships, vessels, or other mobile entities, which may otherwise catch on or come into contact with the submerged datacenter absent the perimeter fence protection. Objects such as these may intentionally or inadvertently result in damage or displacement of the submerged datacenter, or one or more of the datacenter modules, by catching and dragging or otherwise coming into contact with components of the submerged datacenter. An exemplary embodiment of intrusion detection system 200, including a perimeter barrier, may mitigate the risk of underwater intruders attempting to find or access a submerged datacenter by surrounding the datacenter at some distance with the perimeter barrier. Additionally, one or more intrusion detection modules may be implemented on, within, or otherwise coupled to the perimeter barrier, such that any contact between the perimeter barrier and an object is detected by the intrusion detection system.

A perimeter barrier may include cables with high tensile strength, in some examples, which may be placed or installed at the seafloor in order to surround the submerged datacenter. These exemplary cables may be configured to resist attempts to uproot or otherwise pull the cables from the seafloor, for example. In some examples, such resistance may be achieved via attached lead clump weights or restraining elements, implemented at intervals along the cables or other perimeter barrier components. Restraining elements may include, without limitation, embedment of a portion of or component of the perimeter barrier, fluke anchors, or any other suitable means of restraint. By providing resistance to uprooting or displacement of the perimeter barrier, attempts to penetrate or disable the barrier in order to gain access to the datacenter may be mitigated.

In one example, cables may be placed loosely at the seafloor around the datacenter, while in other examples cables may be installed in a specific configuration so as to encompass or surround the datacenter, such as in a ring configuration. A specific configuration for the perimeter barrier may be implemented upon a survey of the seafloor, for example. In other examples, a pattern of interconnected cables may be implemented at a location above the seafloor and secured to the seafloor by connection components, such as hooks or anchors. In an example where the perimeter barrier is elevated above the seafloor, the perimeter barrier may include protruding hooks or snags of its own to capture other anchors or objects used to troll for and snag items on the seafloor.

There may be a variety of data or information sources available to the intrusion detection system. These sources may include, but are not limited to: sensors on, in, or near the datacenter, which exist individually or on collective aggregates (modules) and report on the datacenter (internal environment, servers, network) or its surrounding environment, including activity and health of both the data link and power link to other datacenters or modules of the same datacenter or to external elements such as shore, subsea network, or local power grid; sensors elsewhere, not under control of the datacenter, with the information provided to the intrusion detection system associated with the datacenter via transmission to the datacenter across its data link to the rest of the network; information sources from outside the datacenter from non-sensor sources (e.g., expected locations of ships, weather reports, tsunami alerts, water temperature or current forecasts); analytic products developed from sensor and non-sensor sources from the datacenter and/or from elsewhere, such products created by algorithms or humans or a combination of algorithms and humans. For example, such data sources may provide the identification or location of a ship heading toward the datacenter, or an assessment of the risk that a fishing vessel may pose to the datacenter. All of this data is captured in real-time (or as it arrives) in a database incorporated into or associated with the intrusion detection system associated with the datacenter, and may also be shared with external parties, such as a network operations center or other datacenters, for example.

In parallel with the data capture, algorithms of the intrusion detection system are continually and dynamically updating an assessment or threat model based on all available current data (new data coming in real-time) and historical data (old data and the patterns that are derived from it). This threat assessment or threat model of the intrusion detection system generates a number of analytic products, which may be used locally by algorithms of the intrusion detection system in detecting and identifying potential threats, or shared with external algorithms or humans, or both. Products may include normalcy models, change detection, enhanced sensing and analytics, and threat determination.

Normalcy models may describe a non-threat, normal operating state and/or anticipated sensor readings for time of day, day of week, or time of year. Normalcy models may incorporate all available sensor and non-sensor sources, and may provide a baseline against which anomalous objects and behaviors may be detected, for example.

Change detection is the determination of a deviation, based on incoming data, from the expectations set by the normalcy models. Such changes may be harmless variation or may be indicative of a potential threat or point of interest. Change detection provides the cues for more specific tasks such as: detection of objects, object categorization, identification of anomalous objects, anomalous behavior detection, and object identification. Detection of objects is the process of using the sensors to determine objects near the datacenter and their sensor signatures or characteristics. Object categorization is the process whereby sensor signatures or characteristics, perhaps supported by other data, is used to identify the type or kind of object (e.g., submarine, swimmer, school of fish). Of the categorized objects, some number of those are unexpected and are further characterized as anomalous objects. Anomalous behavior detection is the process whereby categorized objects, which are expected, exhibit unexpected behavior, such as a ship appearing at a different time or location than predicted by the normalcy models, or an unexpected change in ocean current or ambient sound. Object identification is the process of identifying an unexpected object or, alternatively, confirming that an expected object is or is not what was expected.

Enhanced sensing and analytics may be provided based on the determination and execution of something other than the default sensor behavior, to provide greater intensity, more focus, better acuity or range, or other form of directed search or observation to assist with any of the sensing or analytic tasks performed. Threat determination is the process by which all information, from raw data thru analytic products, is used to assess whether the datacenter is under threat, and if so, the kind and severity of threat, and what to do about the perceived threat. Potential threats (e.g., a ship in an unexpected location) may simply be monitored, or an alert sent to the network operations center, or a warning could be issued (e.g., an audible verbal message to divers nearby to stay away).

When an actual threat (e.g., imminent contact with a submersible or divers, loss of power, loss of network connectivity, forecast conflict with fishing vessel's net) is detected a variety of actions can be taken, including: switch to internal battery power; alert a network operations center or other external party, including potentially a large amount of data about what is happening; request guidance from a network operations center or other external party; request an external party to take action (e.g., directly or indirectly alert a shipping company that their vessel is in a no-go zone or the policing authorities of the same); release a buoy or other mechanism which can surface and via radio, audio, or dye in the water warn away an approaching vessel, swimmers, or other intruders; cease computation and (potentially) send critical state from the computation to external parties; cease network traffic with external parties including other datacenter and the network operations center, possibly including an indication that the datacenter is going offline and geo-replication strategies to cope with the loss should be cleanly triggered; render the datacenter's sensitive data (such as all customer data) temporarily inaccessible by deleting all decryption keys (assuming all data is encrypted) from non-volatile memory and either removing power from all volatile memory containing keys or deleting all keys held in volatile storage; and/or render the datacenter's sensitive data permanently inaccessible (destroying it) by flooding the datacenter exposing the internal elements including rotational and solid state disks to the corrosive effects of seawater and, if the internal environment is not highly pressurized, to the high pressure of the ambient external environment; if the normal internal environment is gas or supercritical fluid, this can be effected, for example, by opening a value to the external environment or some other means which effects exchange of fluids with the ocean; if the internal environment is a liquid or liquid-gas combination, opening a value to the external environment will also work, but to achieve a rapid flooding in this case, it may be necessary, for example, to open multiple ports to the ocean or use one or more pumps to effect a rapid exchange of internal and external environments.

Each intrusion detection module 202, 204, 206 may also include one or more sensors, which may be one or more heterogeneous sensors (e.g. one or more different types of sensors, such as a sonar sensor and a temperature sensor for example), one or more homogeneous sensors (one or more sensors of the same type, such as multiple cameras for example), or a combination of one or more heterogeneous and one or more homogenous sensors. For example, intrusion detection module 202 may include multiple sensors of varying different sensor types, and may also include more than one sensor of the same sensor type within a single intrusion detection module. For example, without limitation, the intrusion detection module 202, 204, 206 may include cameras, vibration sensors, acoustic sensors, temperature sensors, pressure sensors, position sensors, fluid flow sensors, and the like, in one integrated sensor module. One or more integrated sensor modules may be implemented at various locations at or adjacent to the submerged datacenter in order to monitor a surrounding environment and detect underwater intrusion attempts.

The intrusion detection system 200 may include one or more cameras for observing an exterior portion of the datacenter modules 102(1)-102(8) and the surrounding area of the datacenter 100. In addition, one or more cameras may be used to observe an interior portion of the datacenter modules 102(1)-102(8). In some embodiments, the cameras may include a means of illumination including but not limited to visible light, infrared (IR) light, or ultraviolet light.

The intrusion detection system 200 may include one or more accelerometers, vibration sensors, or other means of detecting movement, contact with, or force exerted against one or more of the datacenter modules 102(1)-102(8) or other components of the datacenter 100, including, without limitation, pressure vessels, cables, housings, and other components.

The intrusion detection system 200 may include one or more hydrophones or other sound detecting means, which may be used to detect the approach or presence of entities of interest. In some suitable embodiment, sonar, including but not limited to steerable ultrasonic sonar, may be used to detect the geometry of the environment surrounding the datacenter 100 out to a considerable distance, rendering undetected approach by entities of interest difficult.

The intrusion detection system 200 may include one or more other sensors, for example, without limitation, magnetometers that may be used to detect the presence of nearby entities with measurable magnetic properties, water pressure sensors or current profilers that may be used to detect the presence of nearby entities that disturb the water pressure or current profile, and lasers that may be used to detect the presence of nearby entities of interest. The intrusion detection system 200 may include one or more internal sensors or systems, for example, without limitation, acoustic, pressure, vibration, temperature, voltage, current, and fiber network integrity, which may be used to detect intrusion into one or more of the datacenter modules 102(1)-102(8) or power and data connecting cables.

Any number of ways to provide power to the submerged datacenter 100, including the intrusion detection system 200, may be used, including running power from conventional land-based sources, for example, without limitation, running electrical cables from a surface power source to the datacenter 100 and/or the intrusion detection system to establish an umbilical connection. In addition, power may be provided by the use of a surface buoy with a diesel generator located within. However, there are also opportunities to use power sources deployed in water, including ocean-based power sources such as power generated from tidal or ocean currents; in general, it reduces cost to generate power near its usage.

Figure 3A:
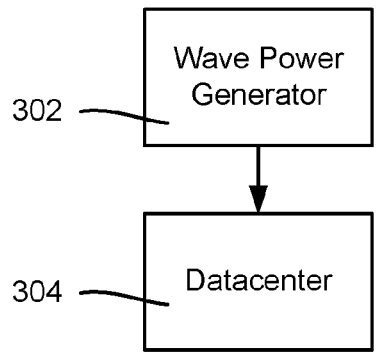
FIGS. 3A-3C are block diagrams representing examples of water-based power sources coupled to provide at least some needed power to a datacenter, according to one or more example implementations.
Figure 3B:
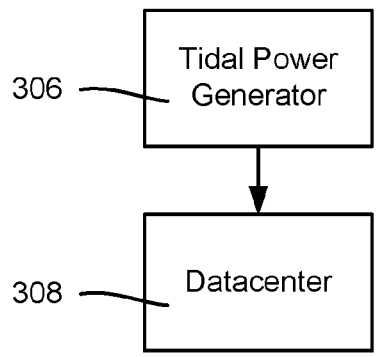

Wave power 302 is exemplified in FIG. 3A as powering a datacenter 304, and tidal power 306 is exemplified in FIG. 3B as powering a datacenter 308. Tidal power 306 is very predictable, whereas wave power 302 may not be as predictable. In the examples shown in FIGS. 3A and 3B, the datacenters 304 and 308 may include one or more datacenter modules. For example, without limitation, the datacenters may include a separate energy generation module, a separate energy storage module, or a single module that combines two or more functions of energy storage, energy generation, and datacenter operations.

Solar power (not shown) is another suitable alternative, although possibly as a supplemental power source to other power sources in datacenters where many megawatts are needed. Nuclear, fusion, and the like may also be used as power sources for datacenters. Indeed, any power source may be used, combined with others, and so on. Power generation capacity may be stored for periods when the energy sources are lower, e.g., when variable power such as based upon tides, ocean currents and/or waves is plentiful, hydrogen may be separated from water for use in fuel cells that are later used for power when needed. If a power connection to the power grid exists, excess power may be sold, and/or if an emergency occurs that knocks out a land-based power source, datacenter consumption may be reduced with the ocean-provided power being output for other purposes. Note that deuterium may be processed near the submerged datacenter and used to provide power; the heat of the datacenter may be used to help in the processing.

Figure 3C:
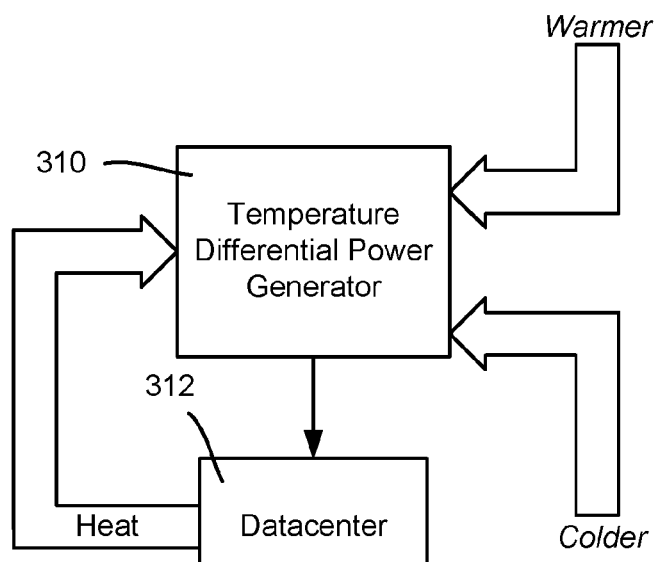

FIG. 3C shows the use of power generation via a temperature differential power generator 310 that is based upon temperature differences, via water near the surface that is warmer than water that is deeper. In FIG. 3C, heat generated by a datacenter 312 may be used to increase the temperature differential, for example.

Figure 4:
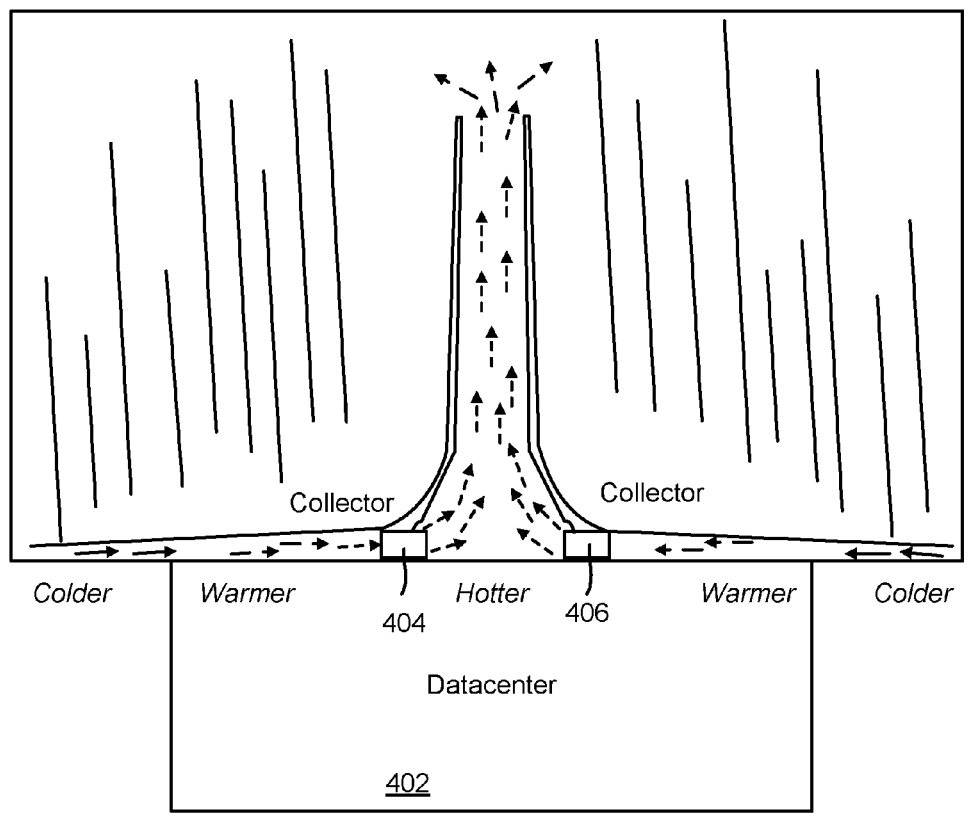
FIG. 4 is an example representation of a submerged datacenter having heat generated thereby used to generate power, according to one or more example implementations.

Another way to use heat is to more directly generate power from it. For example, as shown in FIG. 4, the heat rising from a datacenter 402 may be captured and used to power turbines (e.g., two are shown, labeled 404 and 406). A gas may be selected for use with the datacenter heat and surrounding water temperatures to as to change from gas to a liquid and vice-versa at the desired temperatures, for example. In any event, the datacenter 402 is cooled by the water, whether directly or indirectly by having its heat transferred to another mechanism, such as shown in FIG. 4.

Figure 5:
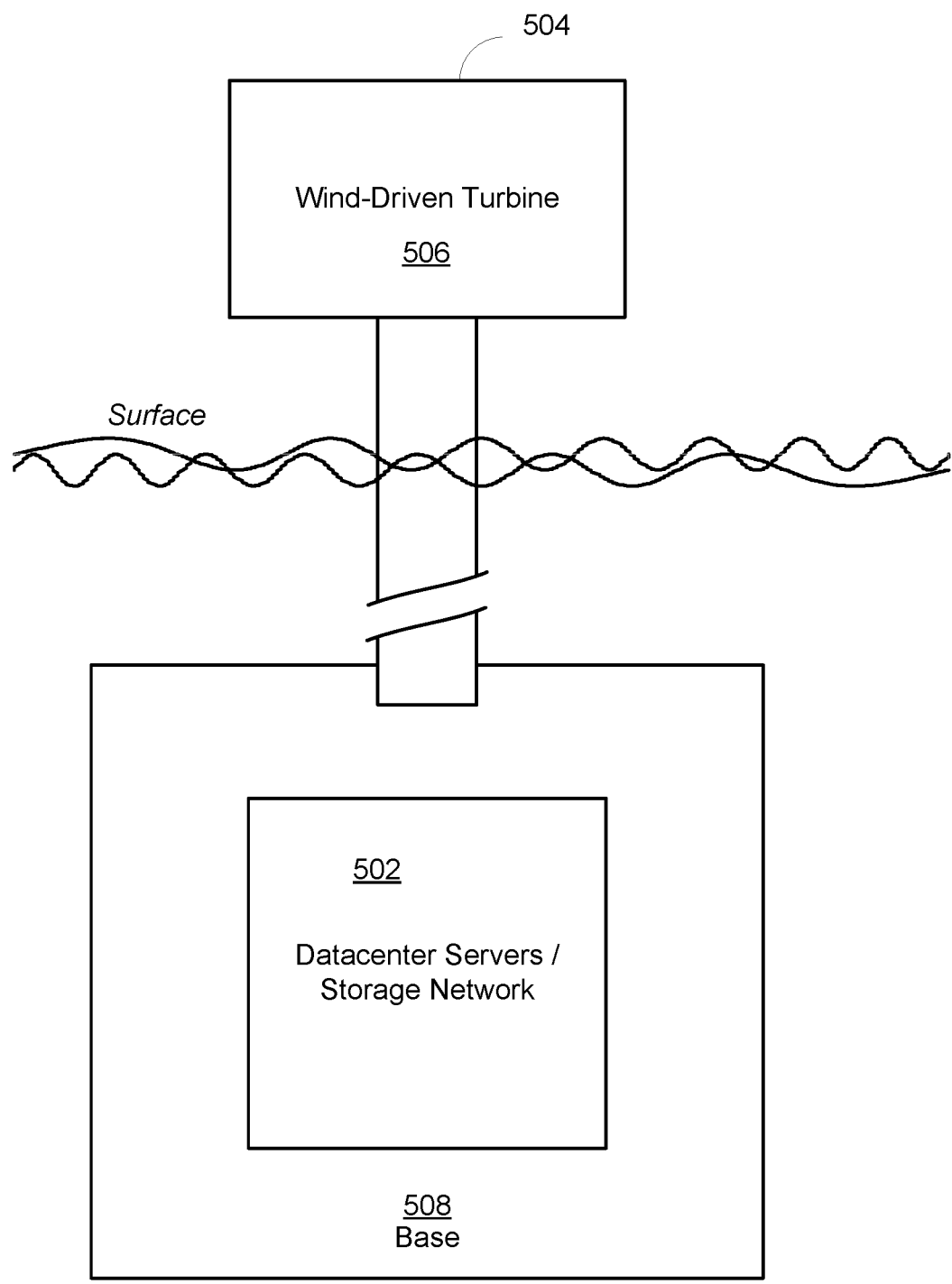
FIG. 5 is an example representation of a datacenter coupled to or incorporated into the base of a wind-driven turbine, according to one or more example implementations.

FIG. 5 shows the deployment of a datacenter 502, or at least part of a datacenter, coupled to an offshore wind turbine power generator 504, the wind turbine power generator 504 comprising a turbine 506 and base 508. If the base 508 is designed to contain water, the datacenter may be incorporated into (submerged in) the base. Note that antennas (not shown) may be arranged near the turbine 504 that may transmit some of the communications, including to land and/or to other modules similarly deployed. Note that any submerged or partially power generation system may likewise have a datacenter coupled thereto or incorporated into it.

Figure 6:
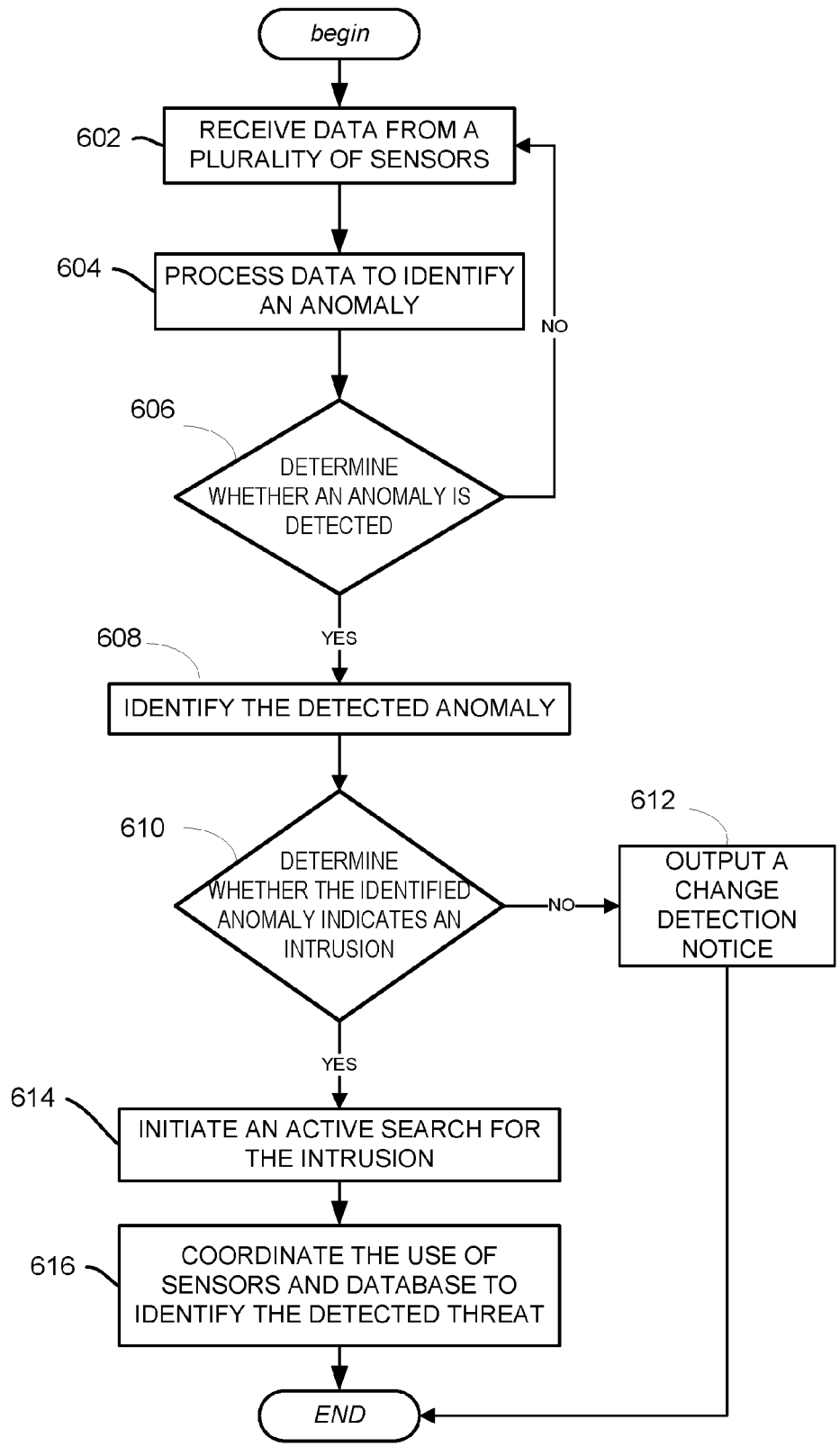
FIG. 6 is a flow diagram showing example operations for detecting intrusion of a submerged datacenter.

FIG. 6 is a flow diagram showing example operations for detecting intrusion into a submerged datacenter, such as datacenter 100 in FIG. 1. It will be understood that any operations depicted are not limited to the exemplary sequence of the diagrams, but rather provide an illustrative example of operations that may occur in any number of varying sequences, or even contemporaneously with some other operations, as provided by aspects of this disclosure. The operations may be implemented in some combination of software and hardware, such as located within one or more of the intrusion detection modules 202, 204, or 206, as depicted in FIG. 2, one or more of datacenter modules 102(1)-102(8), remote facilities including a remote datacenter network operations center or remote datacenter, or some combination thereof, which may interpret and process data from a collection of heterogeneous sources to perform intrusion detection. Sources of data may include the intrusion detection modules 202, 204, 206 under the control of the datacenter 100 (via intrusion detection system 200) as well as external data sources including publicly accessible ocean or weather sensors or reports, Automatic Identification System (AIS) reports, or other available sources.

The process receives data from a plurality of sensors at operation 602. At operation 604 the received data is processed to identify an anomaly. The data received may include information and/or data received from sensors of an intrusion detection system, such as various sensors of intrusion detection modules 202, 204, 206 of FIG. 2, for example. In some examples, only a subset of the received data is processed in order to identify an anomaly at operation 604.

An anomaly may be detected based on or using information that suggests a change in an environment, whether large or small, whether pointing to a distinct cause, or with no clear indication of source or meaning. A change in the surrounding environment may indicate the approach, presence, or action of an entity of interest, including, without limitation, ships, submarines, ROVs, divers, sea mammals, or mechanisms such as winches, anchors, tow cables. A change in the environment may be a distinct observation, such as detecting the signature of a submarine on a hydrophone, an image of a diver swimming nearby, or a change in water temperature, where cloaked or shielded entities are detected by a local change in the underwater temperature. A change in the environment may also be a change in pattern of activity, such as a ship transiting along a different path or at a different time of day than is usual. An anomaly may also be a change in the datacenter 100 connectivity or communications pattern indicative of a cable cut, tap, or other uncharacteristic change.

The process determines whether an anomaly is detected at operation 606 based on processing the received data. If a determination is made that no anomaly is detected, the process returns to operation 602. If a determination is made that an anomaly, i.e., a change in the environment, is detected, the process identifies the detected anomaly at operation 608. The detected anomaly may be identified by a distinct observation, such as detecting the signature of a submarine by a sensor of the intrusion detection system, detecting an image of an object, person, or animal swimming nearby, or detecting a change in water temperature, for example. In other examples, a change in the environment may also be a change in pattern of activity, such as a ship transiting along a different path or at a different time of day than is usual, which may be identified as an anomaly. An anomaly may also be a detected change in datacenter connectivity or communications pattern, which may be indicative of a cable cut, tap, or other uncharacteristic change, for example.

The process determines whether the identified anomaly indicates an intrusion at operation 610. If a determination is made that the identified anomaly does not indicate an intrusion, the process may optionally output a change detection notice at operation 612, with the process terminating thereafter, or alternatively returning to operation 602.

If a determination is made that the identified anomaly indicates an intrusion, the process optionally initiates an active search for the intrusion at operation 614, including coordinated detection among a subset of sensors to find a potential threat to the datacenter 100. The optional active search may be initiated due to an anomaly based on a normalcy model, for example, such as where something expected is undetected or unavailable for identification. An active search may focus one or more sensors of one or more intrusion detection modules on an area of interest, for example, or deploy additional sensors to an area of interest. An intrusion may refer to a physical or virtual attempt to access a datacenter, or data within a datacenter, or some component associated with the datacenter, in some examples. The process coordinates the use of one or more sensors, together with databases, to identify the detected threat at operation 616, with the process terminating thereafter, or alternatively returning to operation 602.

Figure 7:
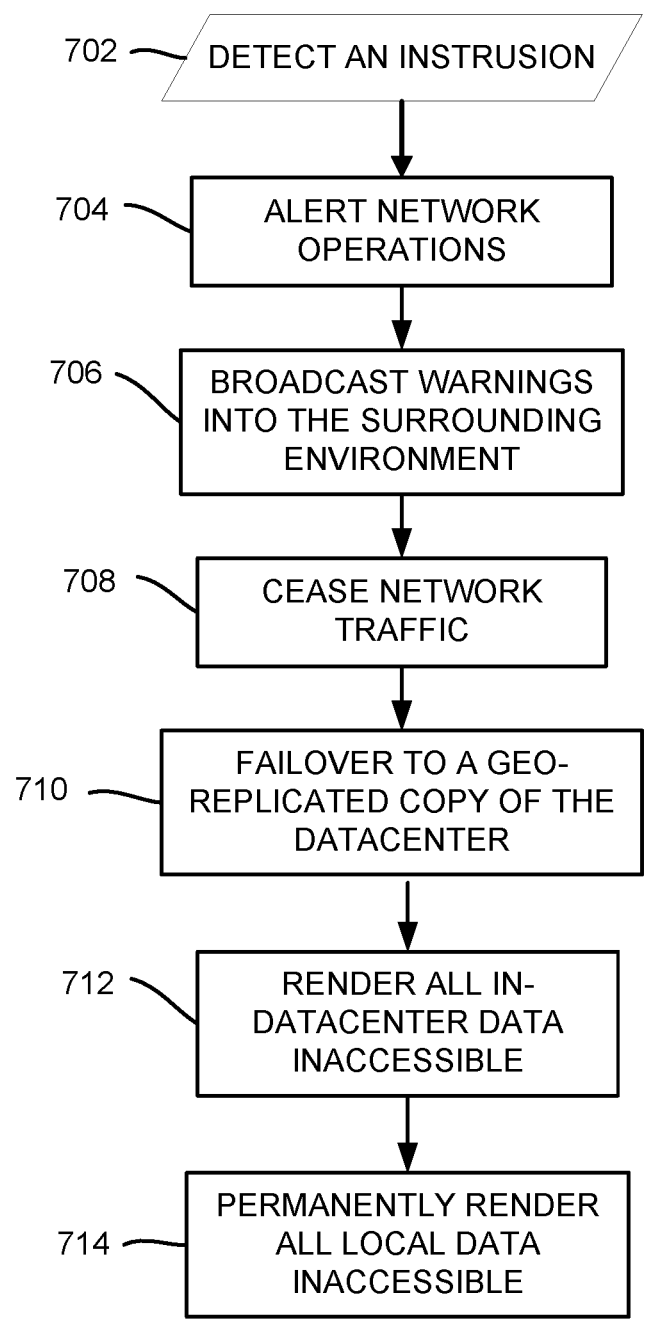
FIG. 7 is a flow diagram showing example operations for performing protective actions upon detection of an intrusion into a submerged datacenter.

FIG. 7 is a flow diagram showing example operations for performing protective actions upon detection of an intrusion into a submerged datacenter, such as datacenter 100 in FIG.

1 for example. The operations may be implemented in some combination of software and hardware. Such action may be taken by any element of the intrusion detection architecture acting individually or collectively including one or more of the intrusion detection modules 202, 204, or 206, one or more of the datacenter modules 102(1)-102(8), or remote facilities.

Upon detection of an intrusion at operation 702, an alert is triggered for network operations at operation 704. The process broadcasts warnings into the surrounding environment at operations 706, such as broadcasting into surrounding water using acoustic emissions. The process ceases network traffic at operation 708. The process may cease network traffic by providing a notification to the datacenter, or to the network operations center, or both, of the alert and detected intrusion, for example, before powering down or blocking network communications.

Upon ceasing network traffic, in order to maintain functionality of the datacenter 100, operations failover to a geo-replicated copy of the datacenter at operation 710. The datacenter rapidly renders all in-datacenter data inaccessible at operation 712, on a temporary basis. For example, any keys that reside within the datacenter may be kept in volatile (non-persistent) memory (e.g., RAM) so that upon loss of power, the keys are no longer accessible to the datacenter. Alternatively, the keys may be in persistent storage, in which case the datacenter may have its own separate power supply configured to last for a short duration of time that provides sufficient time to erase the keys before complete loss of power and shut down is achieved. At operation 714, the datacenter 100 rapidly performs actions to permanently render all local data inaccessible.

Figure 8:
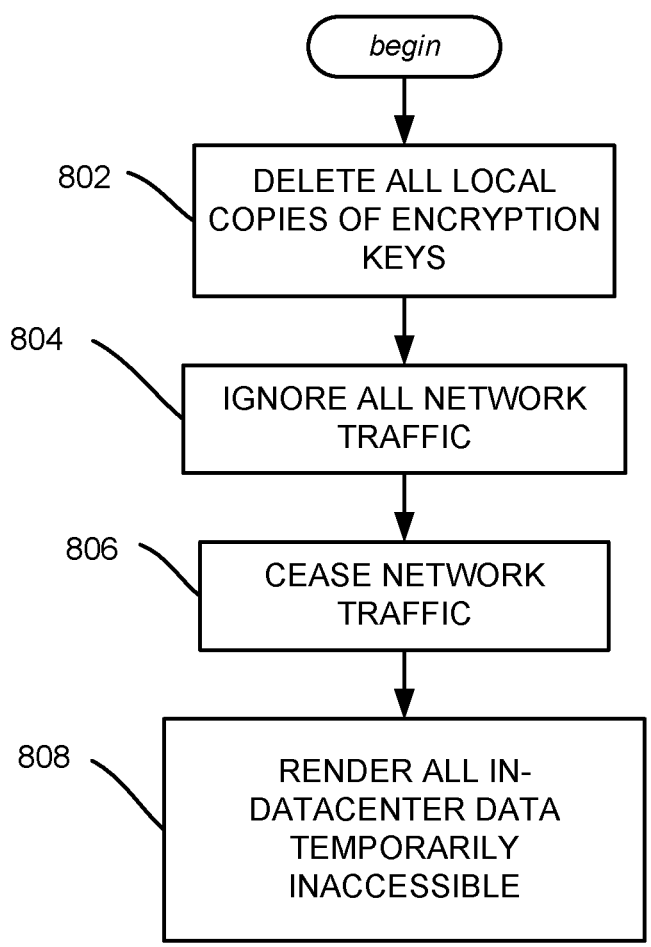
FIG. 8 is a flow diagram showing example operations for rendering all in-datacenter data inaccessible, on a temporary basis, upon detection of an intrusion into a submerged datacenter.

FIG. 8 is a flow diagram showing example operations for rendering all in-datacenter data inaccessible, on a temporary basis, upon detection of an intrusion into a submerged datacenter, such as datacenter 100 in FIG. 1. One or more of the following operations may be performed by the datacenter 100, for example.

The process deletes all local copies of encryption keys at operation 802. The local copies of encryption keys, which may be kept only in non-persistent storage, may be kept in persistent storage, or may be kept in a combination of non-persistent and persistent storage, may be deleted within the time available before backup batteries or capacitors discharge. The process ignores all network traffic at operation 804, pending receipt of a special sequence of packets, including through the use of an encryption one-time pad. At operation 806, the process may power down the datacenter, ceasing all network traffic to and from the datacenter and render all in-datacenter data inaccessible on a temporary basis at operation 808.

Figure 9:
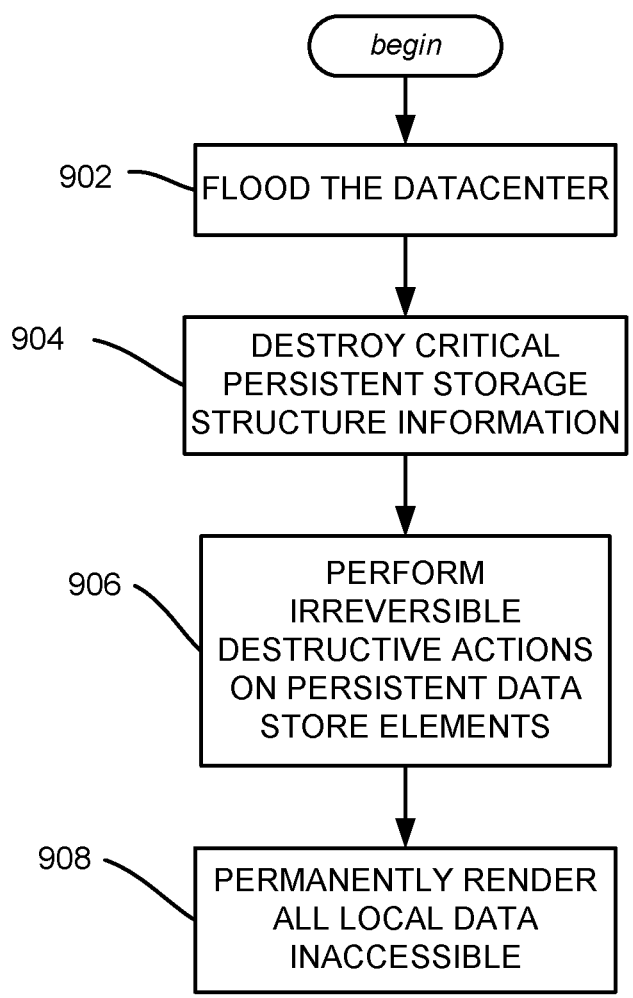
FIG. 9 is a flow diagram showing example operations for permanently rendering all local data inaccessible upon detection of an intrusion into a submerged datacenter.

FIG. 9 is a flow diagram showing example operations for permanently rendering all local data inaccessible upon detection of an intrusion into a submerged datacenter, such as datacenter 100 in FIG. 1. The process floods the datacenter at operation 902 by flooding or otherwise allowing flooding of datacenter modules, such as datacenter modules 102(1)-102(8). The flooding may be orchestrated in any number of suitable operations, such as by causing a valve to open, explosively, mechanically, or otherwise, causing a seal to be ruptured, breaking a valve, pumping water in, or otherwise allowing water to be introduced to a gaseous interior atmosphere of the datacenter in order to pressurize or corrode, or both, the components of the datacenter. In some examples, flooding is achieved by allowing water to displace gas and/or by providing a means to exchange a gas or dielectric fluid within the datacenter for sea water or other water in which the datacenter is submerged.

The process destroys critical persistent storage structure information at operation 904. By virtue of actively flooding or otherwise allowing flooding of the datacenter, the electronic components are physically destroyed, either through the corrosive effect of sea water in instances where submerged at sea, or by pressure of water when submerged at certain depths, or both. At operation 906, the process performs other irreversible destructive actions on persistent data store elements, rendering all local data permanently inaccessible at operation 908.

Additional Examples

Examples of the disclosure provide a technology in which a datacenter is monitored by an intrusion detection system while submerged in water. The intrusion detection system includes a number of sensors for collecting data about the datacenter and its environment. To facilitate trust in the security of the datacenter, the data captured by the intrusion detection system may be made available for review by human personnel, including the owner of the datacenter, customers of the datacenter owner, or the general public, in some examples.

The datacenter may comprise a plurality of modules, each module configured for submersion in water. The modules may be arranged in an array.

The datacenter may receive at least some power generated by the water, e.g., from waves, water current, and/or tide changes. The power generated by the water may be based upon the temperature difference between colder water and warmer water, and at least some heat generated by the datacenter may be used to increase the temperature difference. At least some heat generated by the datacenter may be used to generate power more directly.

The datacenter may be positioned on a platform, and submerged with the platform. The datacenter may be coupled to or incorporated into a submerged based of a wind-driven turbine, or other power generation system.

Alternatively or in addition to the other examples described herein, examples include any combination of the following:
- a power generator, coupled to at least one of the datacenter or the intrusion detection system, that generates power from the movement of the water or air;
- an energy storage module, coupled to the datacenter, that stores energy for use by the datacenter;
- a compound module comprising two or more of the following: a datacenter module, a power generator module, and a power storage module;
- wherein the one or more intrusion detection modules further comprise one or more intrusion detection sensors;
- wherein the one or more intrusion detection modules include at least one of a camera, an accelerometer, a vibration sensor, a hydrophone, a sonar device, a magnetometer, a water pressure sensor, or a laser;
- wherein the one or more intrusion detection modules are coupled directly to the one or more physically separable modules of the datacenter;
- wherein the intrusion detection system includes a perimeter barrier;
- wherein at least a portion of the one or more intrusion detection modules is coupled to the perimeter barrier;
- wherein the one or more intrusion detection modules include at least one of an acoustic sensor, a pressure sensor, a vibration sensor, a temperature sensor, a voltage sensor, a current sensor, or a fiber network integrity sensor;

identifying a change in the environment by a distinct observation;

identifying a change in connectivity of the datacenter to a network;

receiving the data from one or more intrusion detection modules of an intrusion detection system associated with the datacenter;

receiving the data from one or more datacenter modules;

receiving the data from one or more remote facilities, including publicly accessible ocean or weather sensors or reports, or Automatic Identification System (AIS) reports;

broadcasting the warnings into surrounding water of the datacenter using an acoustic emissions component;

wherein rendering the data inaccessible further comprises rendering all in-datacenter data inaccessible, including by performing one or more of deleting all local copies of encryption keys, ignoring all network traffic pending receipt of a special sequence of packets, or powering down the datacenter;

wherein rendering the data inaccessible further comprises permanently rendering all local data inaccessible, including by performing one or more of flooding the datacenter, destroying critical persistent storage structure information, or performing irreversible destructive actions on persistent data store elements;

While the aspects of the disclosure have been described in terms of various examples with their associated operations, a person skilled in the art would appreciate that a combination of operations from any number of different examples is also within scope of the aspects of the disclosure.

Example Datacenter Environment

One of ordinary skill in the art may appreciate that the various embodiments and methods described herein may be implemented in connection with any number of hardware devices, which may be deployed as part of a datacenter or other computing environment, and may be connected to any kind of data store or stores. Thus, the technology is not limited to a datacenter in the conventional sense, but may be used in any situation where computing power is needed near a certain location and heat dissipation is a consideration.

Figure 10:
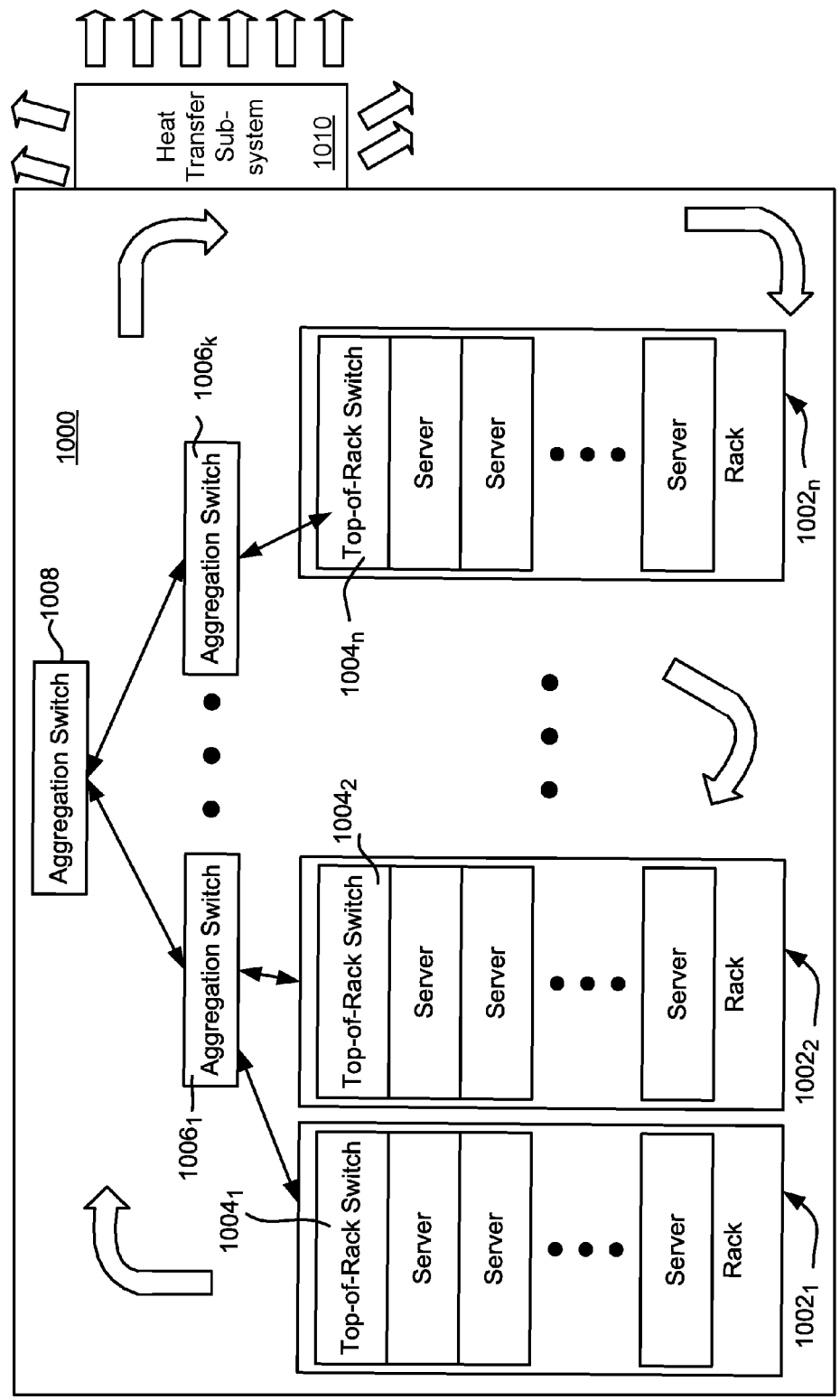
FIG. 10 is a block diagram representing an example submerged datacenter into which one or more aspects of various embodiments described herein may be implemented.

FIG. 10 shows an example submerged datacenter 1000 (or one datacenter module) that is exemplified as having a tree-like topology. A plurality of racks $1002_1$-$1002_n$ each have servers, which communicate through a top of rack switch $1004_1$-$1004_n$. The servers may include storage, or at least part of the storage may be separately located. A typical network has twenty to forty servers per rack, with increasingly powerful links and switches going up the tree. Note that datacenters are not limited to tree-like topologies, but may be used in any topology. A small amount of the computing power may be used to monitor the submerged datacenter sensors, run any fans, pumps and so on, operate an active leveling system, and so on, although this may be done with separate machine logic.

As represented in FIG. 10, each top of rack switch $1004_1$-$1004_n$ is coupled to one another through one or more aggregation switches $1006_1$-$1006_k$. In this way, each server may communicate with any other server, including a server in a different rack. Note that in this example, a higher-level aggregation switch 1008 couples the rack-level aggregation switches $1006_1$-$1006_k$, and there may be one or more additional levels of aggregation switch couplings.

As represented in FIG. 10 by the rounded arrows, the exemplified datacenter has gas and/or dielectric fluid circulated throughout, which may be via pumps, fans and/or natural circulation. A heat transfer subsystem 1010, which may use coils, radiators, fluid pumps, fans and so forth transfers heat away from the datacenter/module to the surrounding water and/or for use in power generation. Note that a module's or datacenter's hull itself may be used as a heat transfer mechanism.

While the aspects of the disclosure are susceptible to various modifications and alternative constructions, certain illustrated embodiments thereof are shown in the drawings and have been described above in detail. It should be understood, however, that there is no intention to limit the disclosure to the specific forms disclosed, but on the contrary, the intention is to cover all modifications, alternative constructions, and equivalents falling within the spirit and scope of the disclosure.

In addition to the various embodiments described herein, it is to be understood that other similar embodiments may be used or modifications and additions may be made to the described embodiment(s) for performing the same or equivalent function of the corresponding embodiment(s) without deviating therefrom. Still further, multiple processing chips or multiple devices may share the performance of one or more functions described herein, and similarly, storage may be effected across a plurality of devices. Accordingly, the disclosure is not to be limited to any single embodiment, but rather is to be construed in breadth, spirit, and scope in accordance with the appended claims.

What is claimed is:

1. A system comprising:

an intrusion detection system coupled to a datacenter configured for operation while submerged in water, the datacenter comprising one or more physically separable modules, the intrusion detection system comprising one or more intrusion detection modules configured to detect underwater intrusion attempts directed towards the datacenter while submerged in the water, the one or more intrusion detection modules further configured to:

responsive to a detection of an intrusion into the datacenter submerged in the water, triggering an alert for network operations;

broadcasting warnings into a surrounding environment;

ceasing network traffic;

failing over to a geo-replicated copy of the datacenter; and permanently rendering local data of the datacenter inaccessible by flooding the datacenter submerged in the water.

2. The system of claim 1 further comprising:

a power generator, coupled to at least one of the datacenter or the intrusion detection system, that generates power from the movement of the water or air.

3. The system of claim 1 further comprising:

an energy storage module, coupled to the datacenter, that stores energy for use by the datacenter.

4. The system of claim 1 further comprising:

a compound module comprising two or more of the following: a datacenter module, a power generator module, and a power storage module.

5. The system of claim 1, wherein the one or more intrusion detection modules further comprise one or more intrusion detection sensors.

6. The system of claim 1, wherein the one or more intrusion detection modules include at least one of a camera, an accelerometer, a vibration sensor, a magnetometer, a water pressure sensor, a hydrophone, a sonar device, or a laser.

7. The system of claim 1, wherein the one or more intrusion detection modules are coupled directly to the one or more physically separable modules of the datacenter.

8. The system of claim 1, wherein the intrusion detection system includes a perimeter barrier.

9. The system of claim 8, wherein at least a portion of the one or more intrusion detection modules is coupled to the perimeter barrier.

10. The system of claim 1, wherein the one or more intrusion detection modules include at least one of an acoustic sensor, a pressure sensor, a vibration sensor, a temperature sensor, a voltage sensor, a current sensor, or a fiber network integrity sensor.

11. In a computing environment, a method for detecting intrusion into a datacenter submerged in water, the method performed at least in part on a processor, the method comprising:
receiving data from a plurality of sensors, wherein the plurality of sensors include at least one of a hydrophone or a sonar device;
determining whether an anomaly is detected using the received data;
responsive to a determination that the anomaly is detected, identifying the anomaly;
determining whether the identified anomaly indicates an underwater intrusion;
responsive to a determination that the detected anomaly is not an intrusion indication, outputting a change detection notice;
responsive to a determination that the detected anomaly indicates the underwater intrusion, initiating a search for the underwater intrusion;
ceasing network traffic;
failing over to a geo-replicated copy of the datacenter; and
permanently rendering local data of the datacenter inaccessible by flooding the datacenter submerged in the water.

12. The method of claim 11, wherein identifying the anomaly further comprises:
identifying a change in the environment by a distinct observation.

13. The method of claim 11, wherein identifying the anomaly further comprises:
identifying a change in connectivity of the datacenter to a network.

14. The method of claim 11, wherein receiving the data from the plurality of sensors further comprises:
receiving the data from one or more intrusion detection modules of an intrusion detection system associated with the datacenter.

15. The method of claim 11, wherein receiving the data from the plurality of sensors further comprises:
receiving the data from one or more datacenter modules.

16. The method of claim 11, wherein receiving the data from the plurality of sensors further comprises:
receiving the data from one or more remote facilities, including publicly accessible ocean or weather sensors or reports, or Automatic Identification System (AIS) reports.

17. In a computing environment, a method for performing protective actions upon detection of an intrusion into a datacenter submerged in water, the method performed at least in part on a processor, the method comprising one or more of:
triggering an alert for network operations;
broadcasting warnings into a surrounding environment;
ceasing network traffic;
failing over to a geo-replicated copy of the datacenter; and
permanently rendering local data of the datacenter inaccessible by flooding the datacenter submerged in the water.

18. The method of claim 17, wherein broadcasting the warnings into the surrounding environment further comprises:
broadcasting the warnings into surrounding water of the datacenter using an acoustic emissions component.

19. The method of claim 17, wherein further rendering the data inaccessible further comprises:
ignoring all network traffic pending receipt of a special sequence of packets.

* * * * *